US00PP22353P2

(12) United States Plant Patent
Kordes

(10) Patent No.: US PP22,353 P2
(45) Date of Patent: Dec. 20, 2011

(54) SHRUB ROSE PLANT NAMED 'KORFOCGRI'

(50) Latin Name: *Rosa hybrida*
Varietal Denomination: KORfocgri

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,198

(22) Filed: Oct. 15, 2010

(51) Int. Cl.
*A01H 5/00* (2006.01)

(52) U.S. Cl. ..... Plt./105

(58) Field of Classification Search ..... Plt./105, Plt./106
See application file for complete search history.

*Primary Examiner* — Kent L Bell

(57) ABSTRACT

A new and distinct variety of rose with long lasting, novel salmon-orange flowers, and attractive foliage with good disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfocgri'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1998. The crossing was between an unnamed seedling and another unnamed seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfocgri'.

SUMMARY OF THE INVENTION

The new rose plant may be distinguished from its seed parent, an unnamed seedling, by the following combination of characteristics:

1. The open flower size of 'KORfocgri' is 80 mm, and the open flower size of the unnamed seedling is 100 mm.
2. 'KORfocgri' is moderately fragrant, while fragrance is absent from the unnamed seedling.

The new rose plant may be distinguished from its pollen parent, an unnamed seedling, by the following combination of characteristics:

1. 'KORfocgri' has, on average, 50 petals, while the unnamed seedling has, on average, 35 petals.

2. The common foliage color of 'KORfocgri' is medium green, while the common foliage color of the unnamed seedling is dark green.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORfocgri' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfocgri' was selected in May, 1999 from the seedling beds to be asexually propagated for further evaluation. The first asexual propagation of 'KORfocgri' was done by budding to seedling understocks in July, 1999 at the inventor's nursery in Offenseth-Sparrieshoop, Germany.

These initial and other subsequent propagations, conducted in controlled environments, demonstrate that 'KORfocgri' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORfocgri'.

DETAILED BOTANICAL DESCRIPTION

The following is a description of 'KORfocgri', as observed growing in September, 2010, in a nursery in Jackson County, Oreg. on plants of five years of age. Color references are made using The Royal Horticultural Society (London, England) Colour Chart, 2001 except where common terms of color are used.

For a comparison, several physical characteristics of the rose variety 'KORtiglo', a rose variety from the same inventor described and illustrated in U.S. Plant Pat. No. 19,385 and issued on Oct. 28, 2008 are compared to 'KORfocgri' in Chart 1.

CHART 1

| Characteristic | 'KORfocgri' | 'KORtiglo' |
|---|---|---|
| Bud form | Pointed ovoid | Globular |
| Average buds per stem | 1-3 | 3-5 |
| General tonality of open flower | Orange-Red Group 30A. | Yellow-Orange Group 20C. |

Parents:

*Seed parent.*—unnamed seedling.

*Pollen parent.*—unnamed seedling.

Classification:

*Botanical classification.*—*Rosa hybrida,* 'KORfocgri'.

*Commercial classification.*—Shrub rose.

FLOWER AND FLOWER BUD

*Blooming habit.*—Recurrent.

*Flower bud.*—Size: Upon opening, 35 mm in length from base of receptacle to end of bud and 20 mm diameter at its widest point. Bud form: Long. Pointed ovoid. Bud color: As sepals first unfold, bud color is Red Group 46C. When ¼ open, the upper surface of petals is Red Group 40A, and the lower surface is Red Group 45D. Sepals: Size: Average 35 mm long×12 mm wide. Shape: Sepals generally subulate. Sepal apex is generally cirrose. Weak foliaceous appendages on three of the five sepals. Base is flat at union with receptacle. Quantity: Five. Margins: With fine hairs. Surface texture: Inner side: Covered in fine hairs. Outer surface: Smooth. Stipitate glands are present. Color: Upper surface Green Group 138C. Lower surface Yellow-Green Group 144A.

*Receptacle.*—Surface: Smooth. Color: Yellow-Green Group 144A. Shape: Funnel. Size: 10 mm (h)×10 mm (w).

*Peduncle.*—Surface: Smooth. With stipitate glands. Length: 45 mm average length. Diameter: 3 mm average diameter. Color: Yellow-Green Group 144A. Strength: Strong. Borne: Singly. 1 - 3 buds per flowering stem.

Flower bloom: Fragrance: Moderate. Duration: On the plant 8-10 days. Long lasting. As a cut flower, 5 to 7 days. Senesced petals drop away cleanly. Size: Medium flowered garden rose. When open, the average flower diameter is 80 mm and the average flower height is 40 mm.

*Form.*—Shape of flower when viewed from the side: Upon opening, upper part: Convex. Upon opening, lower part: Flat. Open flower, upper part: Flattened convex. Open flower, lower part: Flat.

Color:

*Upon opening, petals.*—Outermost petals: Outer Side: Red Group 49D with intonations of Red Group 49A. Inner Side: Red Group 52A. Innermost petals: Outer Side: Orange Group 24C. Inner Side: Orange-Red Group N30A.

*Upon opening, basal petal spots.*—Basal petal spot, outermost petals: Outer Side: Yellow Group 5B. Inner Side: Yellow Group 9B. Basal petal spot, innermost petals: Outer Side: Yellow Group 5C. Inner Side: Yellow Group 9A.

*After opening, petals.*—Outermost petals: Outer Side: Orange Group 27A. Inner Side: Red Group 52B. Innermost petals: Outer Side: Orange Group 27A. Inner Side: Red Group 41B.

*After opening, basal petal spots.*—Basal petal spot, outermost petals: Outer Side: Yellow Group 9C. Inner Side: Yellow Group 9A. Basal petal spot, innermost petals: Outer Side: Yellow Group 9C. Inner Side: Yellow Group 9A. Variegations: None.

General tonality: On open flower Orange-Red Group 30A. No change in the general tonality at the of the 7$^{th}$ day. Afterwards, general tonality is Orange Group 29A.

Petals:

*Petal count.*—Approximately 50 petals under normal conditions.

*Petal reflex.*—Petals reflex slightly.

*Petal edge.*—Entire.

*Petal shape.*—Round. Apex shape is round. Shape of base is rounded.

*Petal size.*—45 mm long; 45 mm wide.

*Thickness.*—Average.

*Petal arrangement.*—Generally in a regular pattern with overlapping edges.

Petaloids: Present.

*Petaloid count.*—Average of 2-5 per flower.

*Petaloid edge.*—Smooth.

*Petaloid texture.*—Smooth.

*Petaloid shape.*—Linear to elliptic.

*Petaloid size.*—Petaloids are 20 mm long and 10 mm wide.

*Petaloid color.*—Color of inner side is Red Group 52B. Color of outer side is Orange Group 27A.

Reproductive organs:

*Pistils.*—Approximately 40 present. Stigmas: Location: Superior in position to anthers. Color: Yellow Group 7C. Styles: Length: 7 mm long. Color: Red Group 40 B. Intonations of Yellow Group 7C.

*Stamens.*—Approximately 90-110 on average and regularly arranged.

*Anthers.*—Size: 2 mm long. Color: Yellow-Orange Group 20A. Pollen: Generally present. Color: Yellow-Orange Group 20A. Filaments: Color: Yellow Group 12A. Length: 12 mm.

THE PLANT

*Plant growth.*—Moderate vigor. Bushy habit. When grown as a budded nursery plant the average plant height is 90 cm and the average plant width is 70 cm.

*Stems.*—Stem color: Young wood: Yellow-Green Group 144A. Older wood: Yellow-Green Group 144A. Stem surface: Young wood: Smooth. Older wood: Smooth.

*Prickles.*—Present. Incidence: 5-8 per 10 cm of mature stem. 8-15 per 10 cm of juvenile stem. Size: Average length: 9 mm. Color: Immature prickles: Gray-Purple Group 186B. Mature prickles: Yellow-Green Group N144C. Senescing to Gray-Brown Group 199D. Shape: Linear. Anthocyanin: Color: Gray-Purple Group 186B.

*Leaves and leaflets.*—Normally 7 leaflets on normal leaves in middle of the stem. Venation pattern: Pyramidal net pattern. Leaf size: 135 mm×105 mm (w). Quantity: Abundant. Texture: Upper side of leaflet: Semi glossy. Smooth. Under side of leaflet: Matte. Smooth. Color, mature foliage: Upper Leaf Surface: Green Group 136A. Lower Leaf Surface: Green Group 136D. Color, juvenile foliage: Upper Leaf Surface: Green Group 137C. Lower Leaf Surface: Yellow-Green Group 144B. Anthocyanin intonation: Present. Location: Intonations present on juvenile leaf margins, developing leaves, peduncles and stems.

*Stipules.*—Size: 25 mm long. 12 mm between the tips of the stipule. Main body of stipule 4 mm in width. Shape: Longitudinally flanged. Stipule color: Yellow Group 144A. Presence of stipitate glands: Present on margins. Margins: Ciliate along the upper margins.

*Petiole.*—Length: 25 mm. Diameter: 3 mm. Petiole color: Yellow Group 144B. Anthocyanin present on juvenile tissue. Color: Gray-Red Group 182B. Underneath: Smooth. Stipitate glands: Lacking.

*Petiole rachis.*—Length: 70 mm. Diameter: 2 mm. Color: Yellow Group 144A. Anthocyanin present on juvenile tissue. Color: Gray-Red Group 182B. Margins: With stipitate glands. Prickles: A few small prickles underneath. Stipitate glands: Limited numbers of stipitate glands on margins.

*Leaflets.*—Size: Average size of the terminal leaflet is 50 mm (l)×35 mm (w). Shape: Ovate. Base: Ovate. Apex: Acute Margins: Serrated. Texture: Leathery.

Hips/seed formation: None observed.

Winter hardiness: To date, the variety has been grown successfully in Zone 5.

Disease resistance: Above average resistance to Powdery mildew (*Sphaerotheca pannosa*), rust (*P. disciflorum*), blackspot (*Diplocarpon rosae*) diseases under normal growing conditions.

I claim:

1. A new and distinct variety of rose plant, as described and illustrated herein.

* * * * *

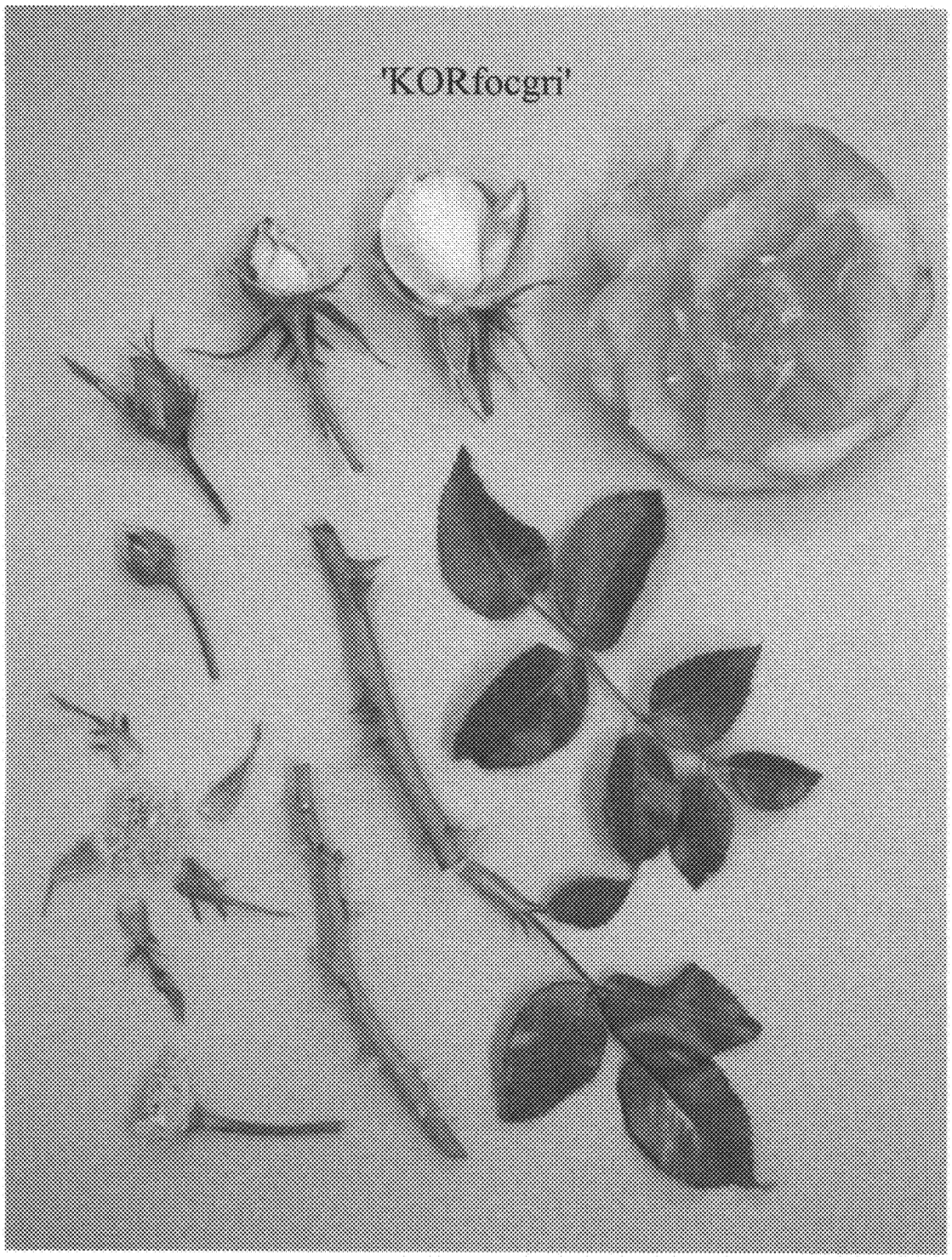
'KORfocgri'